United States Patent [19]

Chak

[11] Patent Number: 4,758,232
[45] Date of Patent: Jul. 19, 1988

[54] SUCTION SYRINGE WITH AN AUTOMATIC LOCKING MEANS

[76] Inventor: Choi K. Chak, 3rd Fl., 5-2, Hsien Te La., Ta Tung St. Sa Lu Cheng, Tai Chung Hsien, Taiwan

[21] Appl. No.: 94,337
[22] Filed: Sep. 8, 1987
[51] Int. Cl.$^4$ ............................................. A61M 5/315
[52] U.S. Cl. ....................................... 604/220; 128/765
[58] Field of Search ............... 604/218, 220, 187, 146, 604/228; 128/765, 763

[56] References Cited

U.S. PATENT DOCUMENTS

| | | | |
|---|---|---|---|
| 2,959,170 | 11/1960 | Laub | 604/220 |
| 3,478,937 | 11/1969 | Solowey | |
| 3,747,812 | 7/1973 | Karman et al. | 604/220 X |
| 4,267,846 | 5/1981 | Kontos | |
| 4,386,606 | 7/1983 | Tretinyak et al. | |
| 4,562,844 | 1/1986 | Carpenter et al. | 604/220 |

Primary Examiner—John D. Yasko
Attorney, Agent, or Firm—Harness, Dickey & Pierce

[57] ABSTRACT

A suction syringe for facilitating blood withdrawing operation by use of a vacuum produced and retained therein in advance is disclosed. This suction syringe comprises a barrel and a plunger slidably positioned in the barrel and is characterized in that the inner periphery of the bore at its proximal open end is provided with at least two chamfered portions and at least two un-chamfered portions in an alternative and equally spaced manner; and that at least two radially deformable elastic portions corresponding, in number and angular positions, to the chamfered portions of the bore in the barrel are integrally formed with the plunger; the elastic portions being depressed and completely received within the bore when the plunger is pushed into the bore of the barrel, and extending radially outwardly and engaging at the un-chamfered portions of the proximal end of the bore when the plunger is pulled rearwardly to a location where the depression force of the bore of the barrel against the elastic portions of the plunger is released; whereby the plunger, when pulled rearwardly to the above location, is locked in same location due to a vacuum produced within the bore, and also due to the engagement of the elastic portions of the plunger with the un-chamfered portions at the proximal end of the bore in the barrel.

1 Claim, 3 Drawing Sheets

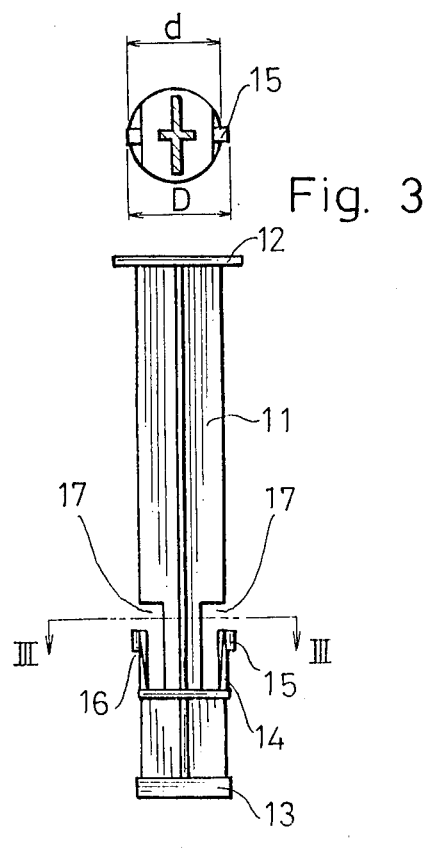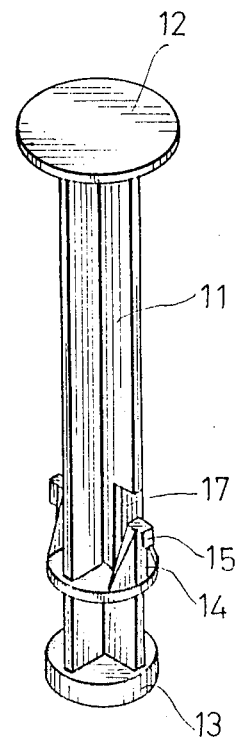
Fig. 3
Fig. 2
Fig. 1

SUCTION SYRINGE WITH AN AUTOMATIC LOCKING MEANS

The present invention relates to a suction syringe in which a vacuum can be produced and automatically retained prior to use so as to facilitate subsequent withdrawing of blood from a patient.

BACKGROUND ART

Applicant is aware of the following pertinent U.S. Pat. Nos

U.S. Pat. No. 3,747,812-Karman et al. (hereinafter referred to as Citation A)

U.S. Pat. No. 3,478,937-Solowey (hereinafter referred to as Citation B)

U.S. Pat. No. 4,267,846-Kontos (hereinafter referred to as Citation C)

U.S. Pat. No. 4,386,606-Tretinyak et al. (hereinafter referred to as Citation D)

U.S. Pat. No. 2,959,170-Laub (hereinafter referred to as Citation E).

The above Citation A discloses a syringe mainly comprising a plunger, a barrel (body) and a pair of clips. Inside of this syringe, a vacuum can be produced before use by pulling out the plunger relative to the barrel and then rotating the plunger to move two brackets provided on the clips into two notches provided in the shaft of the plunger so as to engage the plunger with the clips and thereby retain the produced vacuum. However, as compared with a conventional syringe which mainly comprises only a plunger and a barrel, the construction, assembly and operation of this syringe is more complicated. Consequently, this syringe cannot be manufactured by the same process as that used to produce a conventional syringe and therefore the cost involved in manufacturing this syringe become higher.

That which is disclosed in the above Citation B is a single unit-dose syringe which is used to administer medication into the body cavity, rather than a suction syringe. The plunger as per this Citation is not outwardly returnable after being once depressed. With this syringe, it is impossible to produce and retain a vacuum in the syringe before use. In addition, the locking means shown in FIGS. 4 and 5 of this Citation is made of a pair of pawls, a coil spring, two pins, a spring receiving opening etc., and the construction thereof is quite complicated.

In the above Citation C, a controlled volume blood sampling syringe is disclosed. According to this Citation, the distance which the plunger can move in both inward and outward directions can be controlled. However, with this syringe, it is impossible to produce and retain a vacuum in the barrel before use.

The above Citation D discloses a syringe comprising a plunger, a barrel and a separate locking means for locking the plunger to the barrel. The locking means includes cam means, a handle, and connector means connecting the cam means and the handle. When the locking means is in its locked position, the plunger is forced to one side of the barrel and is pinched or bound between the barrel on one side and cam on the other side, thus locking the plunger against axial movement with respect to the barrel. However, since the locking function is achieved through the deformation of the webs of the plunger and the friction between the cam means and the webs, instead of through more reliable engagement, say, engagement between two step-shaped portions, it is difficult to lock the plunger in an accurate position. Besides, eccentricity of the plunger shank within the barrel might result in the tilt of the piston and destroy the sealing effect of the piston. Furthermore, in addition to that which comprises the aforesaid conventional syringe, the syringe disclosed in Citation D includes a locking means and, therefore, is more expensive to manufacture.

In the above Citation E, a hypodermic syringe, rather than a suction syringe, is disclosed. According to this Citation, before use, the plunger of the syringe is locked in a fixed position by engaging each flange of the barrel, respectively, in a groove formed between a key extending laterally from the proximal end of the plunger and a finger integrally formed with the key. This syringe is intended to be pre-filled with a desired medicament for subsequent use as inoculation against epidemics, rather than to produce and retain a vacuum therein prior to use so as to facilitate a subsequent operation of blood withdrawl.

Although various means, as described above, have been known in the art of syringes for controlling plunger movement relative to the barrel, the art has been deficient in providing a suitable suction syringe which can simultaneously meet all the following requirements such as simple construction, easy operation, low manufacturing cost and accurate locking position of the plunger relative to the barrel.

Therefore, it is toward the solution of this deficiency that the present invention is directed.

SUMMARY OF THE INVENTION

The present invention relates to a suction syringe having a barrel, a plunger axially moveable in the barrel, and locking means integrally formed with the plunger for locking the plunger in a fixed position in the outward movement thereof relative to the barrel.

In a preferred embodiment of the present invention, the locking means is formed of two elastic portions integrally formed at the shank of the plunger. The two elastic portions are depressed inwardly by the inner wall of the barrel when the plunger is pushed into the barrel, and protrude outwardly in radial directions to automatically engage the inner periphery of the open end of the barrel wall when the plunger is pulled out rearwardly to a predetermined position where the depressing force of the barrel wall against the elastic portions is released thereby locking the plunger in same position.

BRIEF DESCRIPTION OF THE DRAWINGS

FIG. 1 is a perspective view of the plunger in a syringe according to a preferred embodiment of the present invention;

FIG. 2 is a front view of the plunger as shown in FIG. 1;

FIG. 3 is a cross-sectional view taken along line III—III of FIG. 2;

DETAILED DESCRIPTION OF THE INVENTION

Figure 6:
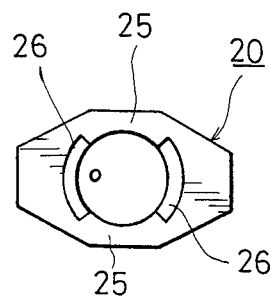
FIG. 6 is a top view of the barrel shown in FIGS. 4 & 5.

While the present invention is satisfied by embodiments in many different forms, there is shown in the drawings and will herein be described in detail a preferred embodiment of the invention, with the understanding that the present disclosure is to be considered as exemplary of the principle of the invention and is not intended to limit the invention to the embodiment illustrated. The scope of the invention will be pointed out in the appended claims.

Figure 5:
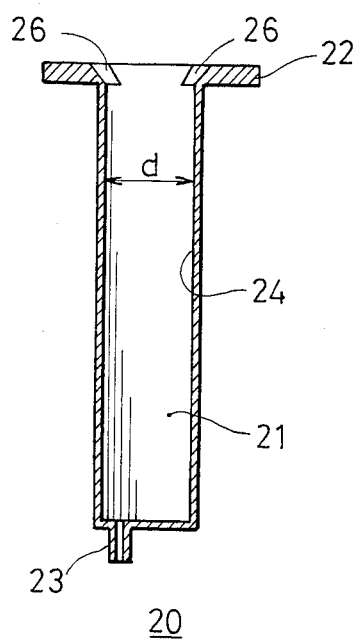
FIG. 5 is a longitudinal sectional view of the barrel as shown in FIG. 4.
Figure 4:
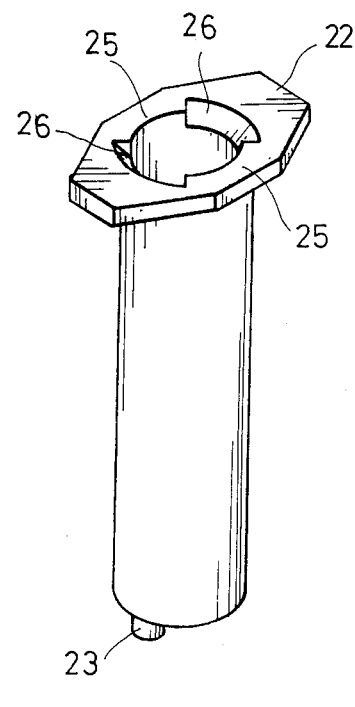
FIG. 4 is a perspective view of the barrel in a syringe according to a preferred embodiment of the present invention.
Figure 7:
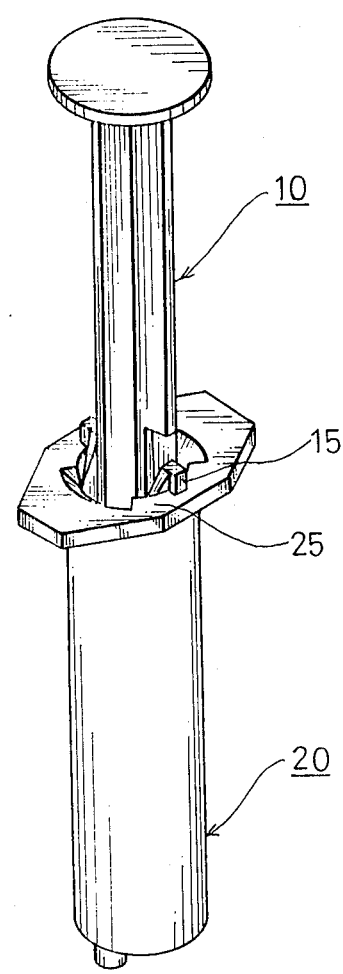
FIG. 7 is a perspective view showing the state in which the plunger of FIG. 1 is locked in a fixed position relative to the barrel of FIG. 4.

Referring now to FIGS. 4 to 6, there is shown a barrel 20 of a preferred syringe of the present invention. The barrel 20 has a bore 21 of an inner diameter d therethrough. The inner periphery 24 of the bore at the proximal end is provided with two chamfered portions 26, 26 and two un-chamfered portions 25, 25, with the chamfered portions 26, 26 and the un-chamfered portions 25, 25 being arranged in an alternative and equally spaced manner along the circumference of the bore 21 as best shown in FIGS. 4 and 6. A flange 22 laterally extends from the proximal end of the barrel 20 for manual grasping. The distal end of the barrel 20 is adapted to be connected to a hollow needle (not shown) at a hollow portion 23.

In FIGS. 1 to 3, there is shown a plunger 10 of a preferred syringe according to the present invention. The plunger 10 is slidably positioned in the bore 21 of the barrel 20. The plunger 10 comprises a piston 13, at its forward end, having a diameter d substantially identical to that of the bore 21 of the barrel 20 and providing a fluid tight seal against the wall of the barrel 20, a cup 12, at its rear end, for manual grasping, and a shank 11 connected at one end to the piston 13 and at the other end to the cap 12. The shank 11 is mostly of cruciform cross section between the piston 13 and the cap 12, with the exception that two notches 17, 17 are formed by partially cutting away two diametrically opposite webs that form the X-shaped form of the shank so as to provide spaces for integrally forming two elastic portions 14, 14 at a proper position along the length of the shank 11. Each elastic portion 14 is radially deformable and has a protrusion 15 at its free end. As best illustrated in FIG. 3, in a non-deformed state, the outermost surfaces of the pair of protrusions 15, 15 are spaced from each other by a distance D larger than the inner diameter d of the aforesaid bore 21 of the barrel 20 (see FIG. 5). Hence, when the plunger 10 is pushed into the bore 21 of the barrel 20, the two protrusions 15, 15 are slightly depressed inwardly so as to be received within the bore 21. However, when the plunger 10 is pulled rearwardly with the two elastic portions 14, 14 being arranged at the same circumferential position as the un-chamfered portions 25, 25 of the barrel 20, the protrusions 15, 15 will protrude radially outwardly once the plunger 10 reaches a position where the depressed force exerted on the protrusions 15, 15 by the inner wall of the barrel 20 is suddenly released, and the step-shaped portions 16, 16 on the undersurface of the protrusions 15, 15 will simultaneously engage at the un-chamfered portions 25, 25 at the proximal end of the bore 21.

In use, the plunger 10, with its piston end directing forward and its two elastic portions 15, 15 aligning respectively with the chamfered portions 26, 26 of the bore 21 in the barrel 20, is first pushed into the bore 21. Then, during the state in which the distal end of a hollow needle (not shown) connected to the hollow portion 23 of the barrel 20 is closed and in which the elastic portions 15, 15 occupy the same circumferential positions as the un-chamfered portions 25, 25 of the barrel 20, the plunger 10 is pulled rearwardly so as to produce a vacuum within the barrel 20 between the undersurface of the piston 13 of the plunger 10 and the closed distal end of the barrel 20. When the plunger 10 is moved rearwardly to a predetermined position, the depression force exerted on the protrusions 15, 15 by the inner wall of the bore 21 of the barrel 20 is suddenly released, and the protrusions 15, 15 will automatically protrude radially outwardly and the step-shaped portions 16, 16 thereof will engage at the un-chamfered portions 25, 25 at the proximal end of the bore 21. The plunger 10 will thus be locked there due to the pressure difference on the two sides of the piston 13 and also due to the mechanical engagement between the protrusions 15, 15 of the plunger 10 and the un-chamfered portions 25, 25 of the barrel 20. Accordingly, a vacuum is retained in the syringe and the unintentional release of the vacuum can be prevented. The needle of the above syringe with a vacuum retained therein can later be penetrated into a blood vessel to automatically withdraw the blood without the necessity of pulling the plunger rearwardly during a blood withdrawing operation. As compared with a conventional syringe, this feature or advantage of the present invention is quite helpful, especially to an inexperienced technician who might tremble in the action of pulling back the plunger and thus cannot withdraw the blood in a stable manner.

It should be noted, from the above description, that the syringe as per the present invention, comprising only a plunger and a barrel, is quite simple in constrution, and thus it may be produced by merely utilizing conventional syringe manufacturing techniques with only the replacement of new forming molds. Hence, the manufacturing cost will not increase in comparison with that of a conventional syringe. In addition to the above-described operation method, capable of automatically locking the plunger in a fixed position and retaining a vacuum in the barrel, the syringe of the present invention can also be operated in a conventional manner if desired.

Summing up the above description with respect to the present invention and to the "Background Art", the following conclusion can be obtained. Namely, the syringes in accordance with Citations B, C and E are not intended to produce and retain a vacuum therein for facilitating the blood withdrawing operation. On the other hand, while the syringes of Citations A and D can be used for similar purposes to the present invention, they are different from and inferior to the syringe of the present invention due to the following reasons. In the case of Citation A, the syringe includes at least two extra clips as compared with a conventional syringe which comprises only a plunger and a barrel. Hence, it is more complicated in construction and is thus impossible to produce using exactly the same manufacturing techniques as those used to produce a conventional syringe. Besides, in the syringe as per Citation A, the locking function of the plunger is achieved by rotating the plunger so as to move and engage two stop brackets mounted to the barrel into two notches provided in the shaft of the plunger. Hence, the plunger cannot be "automatically" locked at a predetermined position. As for the syringe according to Citation D, it possesses the drawback of possible failure in its sealing effect due to the eccentricity of the plunger shank and, consequently, the tilt of the piston, and, also, the drawback of difficulty in locking the plunger in an accurate position such as that necessary for sampling an specific amount of blood. In addition, the necessity of providing an extra locking means will not only increase the manufacturing cost of the syringe, but also make the manufacturing procedure thereof more complicated than the case of the aforesaid conventional syringe.

Accordingly, it can be seen that the present invention has provided an improved syringe which is superior to similar syringes described in the above "Background Art" thanks to its simple construction, its low manufacturing cost and its high degree of accuracy.

Although exemplary embodiment of the present invention has been disclosed and discussed, it will be understood that that the embodiment disclosed may be subjected to various changes, modifications and substitutions without necessarily departing from the spirit of the invention.

What is claimed is:

1. A suction syringe for facilitating blood withdrawing operation by use of a vacuum produced and retained therein in advance, comprising:
   a barrel having a bore therethrough, a distal end of said barrel adapted to be connected to a hollow needle, said bore being open at the proximal end of said barrel; and
   a plunger slidably positioned in said bore providing at its forward end a fluid tight seal against the wall of said barrel, said plunger having a rearward portion extending longitudinally outwardly beyond the proximal end of said barrel;

characterized in that the inner periphery of said bore at said proximal open end is provided with at least two chamfered portions and at least two un-chamfered portions in an alternative and equally spaced manner; and that at least two radially deformable elastic portions corresponding, in number and angular positions, to said chamfered portions of said bore in said barrel are integrally formed with said plunger rearward of said piston; said elastic portions being depressed and completely received within said bore when said plunger is pushed into said bore, and extending radially outwardly and engaging at said un-chamfered portions of the proximal end of said bore when said plunger is pulled rearwardly to a location where the depression force of said bore of said barrel against said elastic portions of said plunger is released;

whereby said plunger, when pulled rearwardly to said location, is locked at said location due to a vacuum produced within said bore between the closed distal end of said bore and said piston of said plunger, and also due to the engagement of said elastic portions of said plunger with said un-chamfered portions at the proximal end of said bore in said barrel.

* * * * *